United States Patent
Nakamura

(10) Patent No.: US 12,417,838 B2
(45) Date of Patent: Sep. 16, 2025

(54) DOCUMENT CREATION SUPPORT APPARATUS, METHOD, AND PROGRAM TO GENERATE MEDICAL DOCUMENT BASED ON MEDICAL IMAGES

(71) Applicant: FUJIFILM Corporation, Tokyo (JP)

(72) Inventor: Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 407 days.

(21) Appl. No.: 17/901,829

(22) Filed: Sep. 1, 2022

(65) Prior Publication Data

US 2023/0005601 A1   Jan. 5, 2023

Related U.S. Application Data

(63) Continuation of application No. PCT/JP2021/011744, filed on Mar. 22, 2021.

(30) Foreign Application Priority Data

Mar. 23, 2020 (JP) .................................. 2020-051707

(51) Int. Cl.
*G16H 30/40* (2018.01)
*G06F 40/56* (2020.01)

(52) U.S. Cl.
CPC .............. *G16H 30/40* (2018.01); *G06F 40/56* (2020.01)

(58) Field of Classification Search
CPC ...................................................... G16H 30/40
See application file for complete search history.

(56) References Cited

U.S. PATENT DOCUMENTS

| 10,769,374 | B1 * | 9/2020 | Chen ....................... G06F 17/16 |
| 2010/0189366 | A1 * | 7/2010 | Iizuka .................... G16H 15/00 382/209 |
| 2015/0235008 | A1 * | 8/2015 | Sasai ...................... G16H 10/60 715/771 |
| 2015/0262014 | A1 * | 9/2015 | Iwamura ................ G16H 50/20 382/128 |
| 2017/0300664 | A1 * | 10/2017 | Matsuki ................. G16H 30/20 |
| 2018/0107636 | A1 * | 4/2018 | Huang .................. G06F 40/166 |
| 2019/0005354 | A1 * | 1/2019 | Nakamura ............. G06N 20/00 |

(Continued)

FOREIGN PATENT DOCUMENTS

| JP | 2001043220 | 2/2001 |
| JP | 2007094515 | 4/2007 |

(Continued)

OTHER PUBLICATIONS

"Notice of Reasons for Refusal of Japan Counterpart Application", issued on Oct. 24, 2023, with English translation thereof, p. 1-p. 8.

(Continued)

*Primary Examiner* — Benjamin O Dulaney
(74) *Attorney, Agent, or Firm* — JCIPRNET

(57) ABSTRACT

A document creation support apparatus includes at least one processor, and the processor generates a sentence related to a property of at least one structure of interest included in an image. The processor determines whether or not a sentence amount of the sentence is a prescribed amount. The processor adjusts the sentence amount such that the sentence amount is the prescribed amount based on a result of the determination.

9 Claims, 12 Drawing Sheets

(56) References Cited

U.S. PATENT DOCUMENTS

| | | | | |
|---|---|---|---|---|
| 2019/0139218 A1* | 5/2019 | Song | .................. | G06N 3/08 |
| 2019/0267132 A1* | 8/2019 | Fuchigami | .............. | G06T 11/60 |
| 2019/0279751 A1* | 9/2019 | Nakamura | ............. | G16H 30/40 |
| 2019/0362835 A1* | 11/2019 | Sreenivasan | ........... | G06N 3/044 |
| 2020/0005942 A1 | 1/2020 | Kawagishi et al. | | |
| 2020/0160982 A1* | 5/2020 | Gurson | .................. | G06N 3/045 |
| 2020/0304822 A1* | 9/2020 | Wang | .................... | G06V 20/41 |
| 2021/0004432 A1* | 1/2021 | Li | ......................... | G06F 40/295 |
| 2021/0241884 A1* | 8/2021 | Swisher | ................. | G06V 10/82 |

FOREIGN PATENT DOCUMENTS

| | | |
|---|---|---|
| JP | 2011087005 | 4/2011 |
| JP | 2018166961 | 11/2018 |
| JP | 2019153250 | 9/2019 |

OTHER PUBLICATIONS

"International Search Report (Form PCT/ISA/210) of PCT/JP2021/011744," mailed on Jun. 15, 2021, with English translation thereof, pp. 1-5.

"Written Opinion of the International Searching Authority (Form PCT/ISA/237)" of PCT/JP2021/011744, mailed on Jun. 15, 2021, with English translation thereof, pp. 1-8.

* cited by examiner

LOCATION OF ABNORMAL SHADOW: UNDER LEFT LUNG PLEURA
SIZE OF ABNORMAL SHADOW: 4.2 cm IN DIAMETER
SHAPE OF BOUNDARY: IRREGULAR
ABSORPTION VALUE: SOLID
SPICULA: +
TUMOR
PLEURAL CONTACT: +
PLEURAL INVAGINATION: +
PLEURAL INFILTRATION: -
CAVITY: -
CALCIFICATION: -

FIG. 6

51
21 mm-SIZED IRREGULAR SOLID NODULE IS FOUND IN LEFT LOWER LOBE S6. IT IS LOBULAR AND HAS CLEAR BOUNDARY. CALCIFICATION IS FOUND INSIDE, BUT CAVITIES AND AIR BRONCHOGRAMS ARE NOT INCLUDED. NODULE IS IN CONTACT WITH PLEURA.

52
21 mm-SIZED IRREGULAR SOLID NODULE IS FOUND IN LEFT LOWER LOBE S6.

53
21 mm-SIZED IRREGULAR SOLID NODULE IS FOUND IN LEFT LOWER LOBE S6. IT IS LOBULAR AND HAS CLEAR BOUNDARY.

54
21 mm-SIZED IRREGULAR SOLID NODULE IS FOUND IN LEFT LOWER LOBE S6. IT IS LOBULAR AND HAS CLEAR BOUNDARY. CALCIFICATION IS FOUND INSIDE. NODULE IS IN CONTACT WITH PLEURA.

FIG. 7

61
21 mm-SIZED IRREGULAR SOLID NODULE IS FOUND IN LEFT LOWER LOBE S6.

62
21 mm-SIZED IRREGULAR SOLID NODULE IS FOUND IN LEFT LOWER LOBE S6. IT IS LOBULAR AND HAS CLEAR BOUNDARY. CALCIFICATION IS FOUND INSIDE. NODULE IS IN CONTACT WITH PLEURA.

63
21 mm-SIZED IRREGULAR SOLID NODULE IS FOUND IN LEFT LOWER LOBE S6. IT IS LOBULAR AND HAS CLEAR BOUNDARY. CALCIFICATION IS FOUND INSIDE, BUT CAVITIES AND AIR BRONCHOGRAMS ARE NOT INCLUDED. NODULE IS IN CONTACT WITH PLEURA.

THERE IS SOLID NODULE WITH IRREGULARITIES IN LEFT LUNG S3. IT IS ACCOMPANIED BY SPICULA. IN ADDITION, THERE IS SOLID NODULE WITH IRREGULARITIES IN RIGHT LUNG S7.

66

THERE ARE SOLID NODULES WITH IRREGULARITIES IN LEFT LUNG S3 AND RIGHT LUNG S7.

FIG. 9

ABNORMAL SHADOW A

71A 21 mm-SIZED IRREGULAR SOLID NODULE IS FOUND IN LEFT LOWER LOBE S6.

71B 21 mm-SIZED IRREGULAR SOLID NODULE IS FOUND IN LEFT LOWER LOBE S6.
IT IS LOBULAR AND HAS CLEAR BOUNDARY.

71C 21 mm-SIZED IRREGULAR SOLID NODULE IS FOUND IN LEFT LOWER LOBE S6.
IT IS LOBULAR AND HAS CLEAR BOUNDARY.
CALCIFICATION IS FOUND INSIDE, BUT CAVITIES AND AIR BRONCHOGRAMS
ARE NOT INCLUDED.
NODULE IS IN CONTACT WITH PLEURA.

ABNORMAL SHADOW B

72A 48 mm-SIZED IRREGULAR TUMOR IS FOUND IN RIGHT LOWER LOBE S8.

72B 48 mm-SIZED IRREGULAR TUMOR IS FOUND IN RIGHT LOWER LOBE S8.
MARGINS ARE SERRATED, WITH SPICULA AND PLEURAL INVAGINATION.

72C 48 mm-SIZED IRREGULAR TUMOR IS FOUND IN RIGHT LOWER LOBE S8.
MARGINS ARE SERRATED, WITH SPICULA AND PLEURAL INVAGINATION.
AIR BRONCHOGRAMS, CALCIFICATION, AND CAVITIES ARE FOUND INSIDE.
TUMOR IS IN CONTACT WITH PLEURA.

21 mm-SIZED IRREGULAR SOLID NODULE IS FOUND IN LEFT LOWER LOBE S6.
IT IS LOBULAR AND HAS CLEAR BOUNDARY. CALCIFICATION IS FOUND INSIDE,
BUT CAVITIES AND AIR BRONCHOGRAMS ARE NOT INCLUDED.
NODULE IS IN CONTACT WITH PLEURA.
48 mm-SIZED IRREGULAR TUMOR IS FOUND IN RIGHT LOWER LOBE S8.
MARGINS ARE SERRATED, WITH SPICULA AND PLEURAL INVAGINATION.
AIR BRONCHOGRAMS, CALCIFICATION, AND CAVITIES ARE FOUND INSIDE.
TUMOR IS IN CONTACT WITH PLEURA.

74

21 mm-SIZED IRREGULAR SOLID NODULE IS FOUND IN LEFT LOWER LOBE S6.
48 mm-SIZED IRREGULAR TUMOR IS FOUND IN RIGHT LOWER LOBE S8.
MARGINS ARE SERRATED, WITH SPICULA AND PLEURAL INVAGINATION.
AIR BRONCHOGRAMS, CALCIFICATION, AND CAVITIES ARE FOUND INSIDE.
TUMOR IS IN CONTACT WITH PLEURA.

DOCUMENT CREATION SUPPORT APPARATUS, METHOD, AND PROGRAM TO GENERATE MEDICAL DOCUMENT BASED ON MEDICAL IMAGES

CROSS REFERENCE TO RELATED APPLICATIONS

The present application is a Continuation of PCT International Application No. PCT/JP2021/011744, filed on Mar. 22, 2021, which claims priority to Japanese Patent Application No. 2020-051707, filed on Mar. 23, 2020. Each application above is hereby expressly incorporated by reference, in its entirety, into the present application.

BACKGROUND

Technical Field

The present disclosure relates to a document creation support apparatus, method, and program that support creation of documents such as medical documents.

Related Art

In recent years, advances in medical devices, such as computed tomography (CT) apparatuses and magnetic resonance imaging (MRI) apparatuses, have enabled image diagnosis using high-resolution medical images with higher quality. In particular, since a region of a lesion can be accurately specified by image diagnosis using CT images, MRI images, and the like, appropriate treatment is being performed based on the specified result.

In addition, image diagnosis is also made by analyzing a medical image via computer-aided diagnosis (CAD) using a learning model in which machine learning is performed by deep learning or the like, discriminating properties such as the shape, density, position, and size of structures of interest such as abnormal shadows included in the medical images, and acquiring them as an analysis result. The analysis result acquired by CAD is associated with examination information such as a patient name, gender, age, and a modality that has acquired the medical image, and is saved in a database. The medical image and the analysis result are transmitted to a terminal of a radiologist who interprets the medical images. The radiologist interprets the medical image by referring to the transmitted medical image and analysis result and creates an interpretation report, in his or her own terminal.

Meanwhile, with the improvement of the performance of the CT apparatus and the MRI apparatus described above, the number of medical images to be interpreted is also increasing. However, since the number of radiologists has not kept up with the number of medical images, it is desired to reduce the burden of the image interpretation work of the radiologists. Therefore, various methods have been proposed to support the creation of medical documents such as interpretation reports. For example, JP2019-153250A proposes various methods for generating a sentence to be included in an interpretation report based on keywords input by a radiologist and on information indicating a property of a structure of interest (hereinafter referred to as property information) included in an analysis result of a medical image. In the methods described in JP2019-153250A, a sentence relating to medical care (hereinafter referred to as a medical sentence) is created by using a learning model in which machine learning is performed, such as a recurrent neural network trained to generate a sentence from characters representing the input property information. By automatically generating the medical sentence as in the method described in JP2019-153250A, it is possible to reduce a burden on a radiologist at the time of creating a medical document such as an interpretation report.

Incidentally, as described above, if the sentence generated by the learning model is too long, the burden on a reader such as an attending physician who reads the sentence becomes large. Conversely, if the medical sentence is too short, the reader is worried whether the medical sentence includes necessary information about the structure of interest included in the medical image.

SUMMARY OF THE INVENTION

The present disclosure has been made in consideration of the above circumstances, and an object thereof is to enable the generation of sentences with an appropriate amount of information.

According to an aspect of the present disclosure, there is provided a document creation support apparatus comprising at least one processor, in which the processor is configured to generate a sentence related to a property of at least one structure of interest included in an image, determine whether or not a sentence amount of the sentence is a prescribed amount, and adjust the sentence amount such that the sentence amount is the prescribed amount based on a result of the determination.

For the "sentence amount", for example, the number of characters, the number of lines, the number of paragraphs, and the like of the sentence can be used.

The "prescribed amount" may be a constant value or a value having a range. The range may have only an upper limit value, may have only a lower limit value, or may have both an upper limit value and a lower limit value.

In the document creation support apparatus according to the aspect of the present disclosure, the processor may be configured to adjust the sentence amount by selecting a property to be described in the sentence from among one or more properties of the structure of interest.

In the document creation support apparatus according to the aspect of the present disclosure, the processor may be configured to generate the sentence including a description regarding each of one or more properties specified for the structure of interest, and adjust the sentence amount by deleting, from the sentence, a description regarding a negative property among descriptions regarding each of a plurality of properties included in the sentence.

In the document creation support apparatus according to the aspect of the present disclosure, the processor may be configured to generate, for a plurality of structures of interest included in the image, a plurality of sentences describing properties of each of the structures of interest, and adjust the sentence amount of the sentence for at least one of the plurality of structures of interest such that a total amount of the sentence generated for each of the plurality of structures of interest is the prescribed amount.

In the document creation support apparatus according to the aspect of the present disclosure, the processor may be configured to adjust the sentence amount by integrating common descriptions among the descriptions regarding each of the plurality of structures of interest included in the sentence.

In the document creation support apparatus according to the aspect of the present disclosure, the processor may be configured to generate, for a plurality of structures of interest included in the image, a plurality of candidate sentences describing properties of each of the structures of interest, and adjust, for each of the plurality of structures of interest, the sentence amount by selecting a combination in which a sentence amount of a sentence including a selected candidate sentence is the prescribed amount from combinations of selecting one candidate sentence from among the plurality of candidate sentences.

In the document creation support apparatus according to the aspect of the present disclosure, the processor may be configured to display the sentence on a display.

In the document creation support apparatus according to the aspect of the present disclosure, the image may be a medical image, and the sentence may be a medical sentence related to the structure of interest included in the medical image.

According to another aspect of the present disclosure, there is provided a document creation support method comprising: generating a sentence related to a property of at least one structure of interest included in an image; determining whether or not a sentence amount of the sentence is a prescribed amount; and adjusting the sentence amount such that the sentence amount is the prescribed amount based on a result of the determination.

In addition, a program for causing a computer to execute the document creation support method according to the aspect of the present disclosure may be provided.

According to the aspects of the present disclosure, it is possible to generate medical sentences with an appropriate amount of information.

BRIEF DESCRIPTION OF THE DRAWINGS

FIG. 4 is a diagram for describing property information derived by an image analysis unit.

FIG. 6 is a diagram showing an example of medical sentences and medical sentences in which a sentence amount is adjusted.

FIG. 7 is a diagram showing an example of medical sentences and medical sentences in which a sentence amount is adjusted.

FIG. 8 is a diagram showing an example of medical sentences and medical sentences in which a sentence amount is adjusted.

FIG. 9 is a diagram showing an example of medical sentences and medical sentences in which a sentence amount is adjusted.

FIG. 10 is a diagram showing an example of medical sentences and medical sentences in which a sentence amount is adjusted.

DETAILED DESCRIPTION

Figure 1:
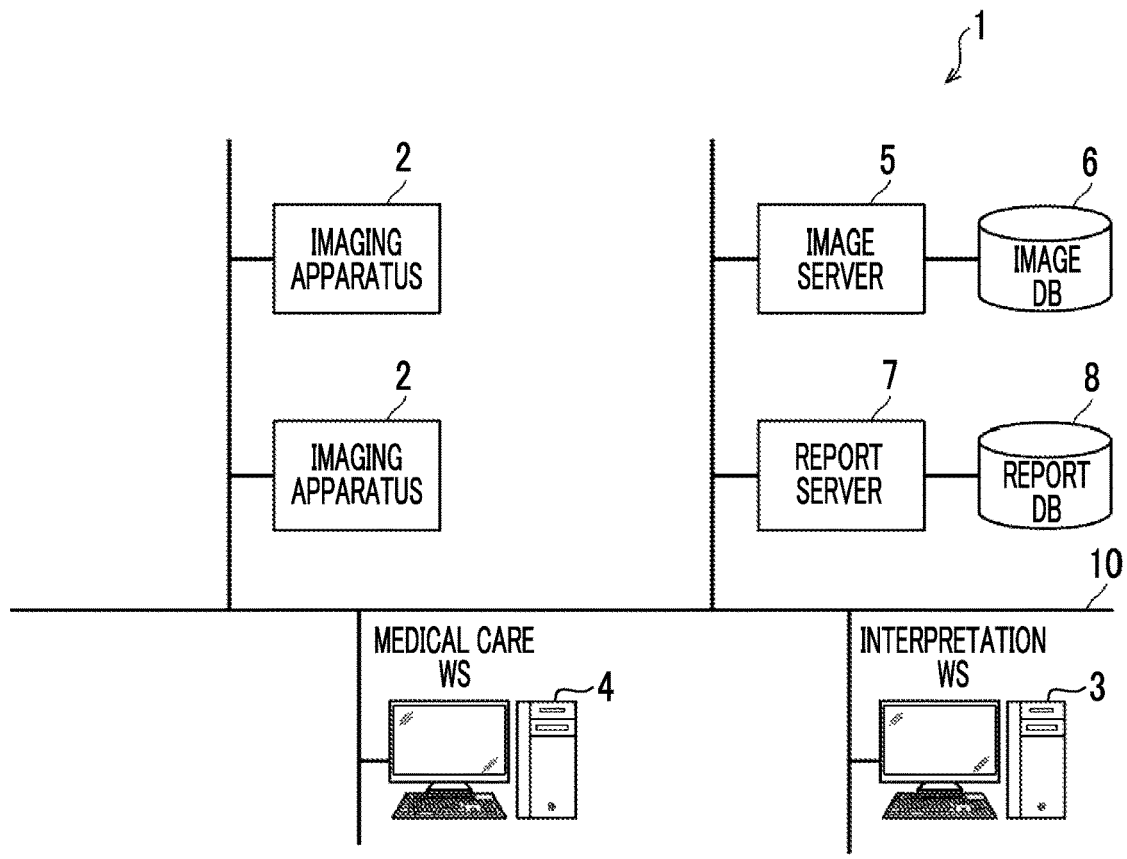
FIG. 1 is a diagram showing a schematic configuration of a medical information system to which a document creation support apparatus according to an embodiment of the present disclosure is applied.

Hereinafter, embodiments of the present disclosure will be described with reference to the drawings. First, a configuration of a medical information system 1 to which a document creation support apparatus according to the present embodiment is applied will be described. FIG. 1 is a diagram showing a schematic configuration of the medical information system 1. The medical information system 1 shown in FIG. 1 is, based on an examination order from a doctor in a medical department using a known ordering system, a system for imaging an examination target part of a subject, storing a medical image acquired by the imaging, interpreting the medical image by a radiologist and creating an interpretation report, and viewing the interpretation report and observing the medical image to be interpreted in detail by the doctor in the medical department that is a request source.

As shown in FIG. 1, in the medical information system 1, a plurality of imaging apparatuses 2, a plurality of interpretation workstations (WSs) 3 that are interpretation terminals, a medical care WS 4, an image server 5, an image database (hereinafter referred to as an image DB) 6, a report server 7, and a report database (hereinafter referred to as a report DB) 8 are communicably connected to each other through a wired or wireless network 10.

Each apparatus is a computer on which an application program for causing each apparatus to function as a component of the medical information system 1 is installed. The application program is stored in a storage apparatus of a server computer connected to the network 10 or in a network storage in a state in which it can be accessed from the outside, and is downloaded to and installed on the computer in response to a request. Alternatively, the application program is recorded on a recording medium, such as a digital versatile disc (DVD) and a compact disc read only memory (CD-ROM), and distributed, and is installed on the computer from the recording medium.

The imaging apparatus 2 is an apparatus (modality) that generates a medical image showing a diagnosis target part of the subject by imaging the diagnosis target part. Specifically, examples of the modality include a simple X-ray imaging apparatus, a CT apparatus, an MRI apparatus, a positron emission tomography (PET) apparatus, and the like. The medical image generated by the imaging apparatus 2 is transmitted to the image server 5 and is saved in the image DB 6.

The interpretation WS 3 is a computer used by, for example, a radiologist of a radiology department to interpret a medical image and to create an interpretation report, and encompasses a document creation support apparatus 20 according to the present embodiment. In the interpretation WS 3, a viewing request for a medical image to the image server 5, various image processing for the medical image received from the image server 5, display of the medical image, input reception of comments on findings regarding the medical image, and the like are performed. In the interpretation WS 3, an analysis process for medical images and input comments on findings, support for creating an interpretation report based on the analysis result, a registration request and a viewing request for the interpretation report to the report server 7, and display of the interpretation report received from the report server 7 are performed. The above processes are performed by the interpretation WS 3 executing software programs for respective processes.

The medical care WS 4 is a computer used by a doctor in a medical department to observe an image in detail, view an interpretation report, create an electronic medical record, and the like, and is configured to include a processing apparatus, a display apparatus such as a display, and an input apparatus such as a keyboard and a mouse. In the medical care WS 4, a viewing request for the image to the image server 5, display of the image received from the image server 5, a viewing request for the interpretation report to the report server 7, and display of the interpretation report received from the report server 7 are performed. The above processes are performed by the medical care WS 4 executing software programs for respective processes.

The image server 5 is a general-purpose computer on which a software program that provides a function of a database management system (DBMS) is installed. The image server 5 comprises a storage in which the image DB 6 is configured. This storage may be a hard disk apparatus connected to the image server 5 by a data bus, or may be a disk apparatus connected to a storage area network (SAN) or a network attached storage (NAS) connected to the network 10. In a case where the image server 5 receives a request to register a medical image from the imaging apparatus 2, the image server 5 prepares the medical image in a format for a database and registers the medical image in the image DB 6.

Image data of the medical image acquired by the imaging apparatus 2 and accessory information are registered in the image DB 6. The accessory information includes, for example, an image identification (ID) for identifying each medical image, a patient ID for identifying a subject, an examination ID for identifying an examination, a unique ID (unique identification (UID)) allocated for each medical image, examination date and examination time at which a medical image is generated, the type of imaging apparatus used in an examination for acquiring a medical image, patient information such as the name, age, and gender of a patient, an examination part (an imaging part), imaging information (an imaging protocol, an imaging sequence, an imaging method, imaging conditions, the use of a contrast medium, and the like), and information such as a series number or a collection number in a case where a plurality of medical images are acquired in one examination.

In addition, in a case where the viewing request from the interpretation WS 3 and the medical care WS 4 is received through the network 10, the image server 5 searches for a medical image registered in the image DB 6 and transmits the searched for medical image to the interpretation WS 3 and to the medical care WS 4 that are request sources.

The report server 7 incorporates a software program for providing a function of a database management system to a general-purpose computer. In a case where the report server 7 receives a request to register the interpretation report from the interpretation WS 3, the report server 7 prepares the interpretation report in a format for a database and registers the interpretation report in the report DB 8.

In the report DB 8, an interpretation report including at least the comments on findings created in the interpretation WS 3 is registered. The interpretation report may include, for example, information such as a medical image to be interpreted, an image ID for identifying the medical image, a radiologist ID for identifying the radiologist who performed the interpretation, a lesion name, lesion position information, information for accessing a medical image including a specific region, and property information.

Further, in a case where the report server 7 receives the viewing request for the interpretation report from the interpretation WS 3 and the medical care WS 4 through the network 10, the report server 7 searches for the interpretation report registered in the report DB 8, and transmits the searched for interpretation report to the interpretation WS 3 and to the medical care WS 4 that are request sources.

In the present embodiment, it is assumed that the medical image is a three-dimensional CT image consisting of a plurality of tomographic images with a lung as a diagnosis target, and an interpretation report including, as comments on findings, a medical sentence on a structure of interest such as an abnormal shadow included in the lung is created by interpreting the CT image. The medical image is not limited to the CT image, and any medical image such as an MRI image and a simple two-dimensional image acquired by a simple X-ray imaging apparatus can be used.

The network 10 is a wired or wireless local area network that connects various apparatuses in a hospital to each other. In a case where the interpretation WS 3 is installed in another hospital or clinic, the network 10 may be configured to connect local area networks of respective hospitals through the Internet or a dedicated line.

Figure 2:
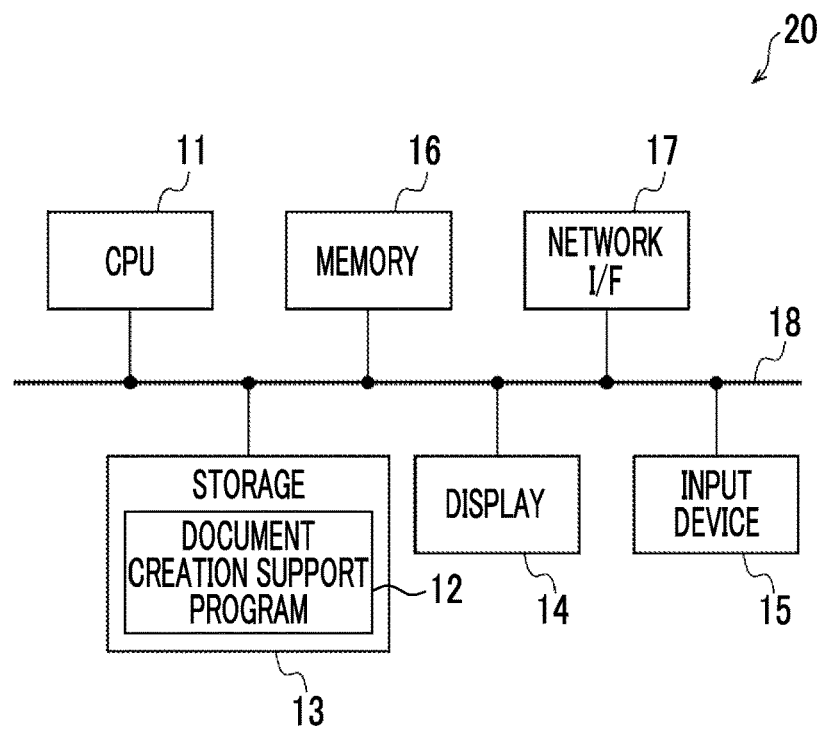
FIG. 2 is a diagram showing a schematic configuration of the document creation support apparatus according to the present embodiment.

Next, the document creation support apparatus according to the present embodiment will be described. FIG. 2 illustrates a hardware configuration of the document creation support apparatus according to the present embodiment. As shown in FIG. 2, the document creation support apparatus 20 includes a central processing unit (CPU) 11, a non-volatile storage 13, and a memory 16 as a temporary storage area. Further, the document creation support apparatus 20 includes a display 14 such as a liquid crystal display, an input device 15 such as a keyboard and a mouse, and a network interface (I/F) 17 connected to the network 10. The CPU 11, the storage 13, the display 14, the input device 15, the memory 16, and the network I/F 17 are connected to a bus 18. The CPU 11 is an example of a processor in the present disclosure.

The storage 13 is realized by a hard disk drive (HDD), a solid state drive (SSD), a flash memory, and the like. A document creation support program is stored in the storage 13 as a storage medium. The CPU 11 reads a document creation support program 12 from the storage 13, loads the read document creation support program 12 into the memory 16, and executes the loaded document creation support program 12.

Figure 3:
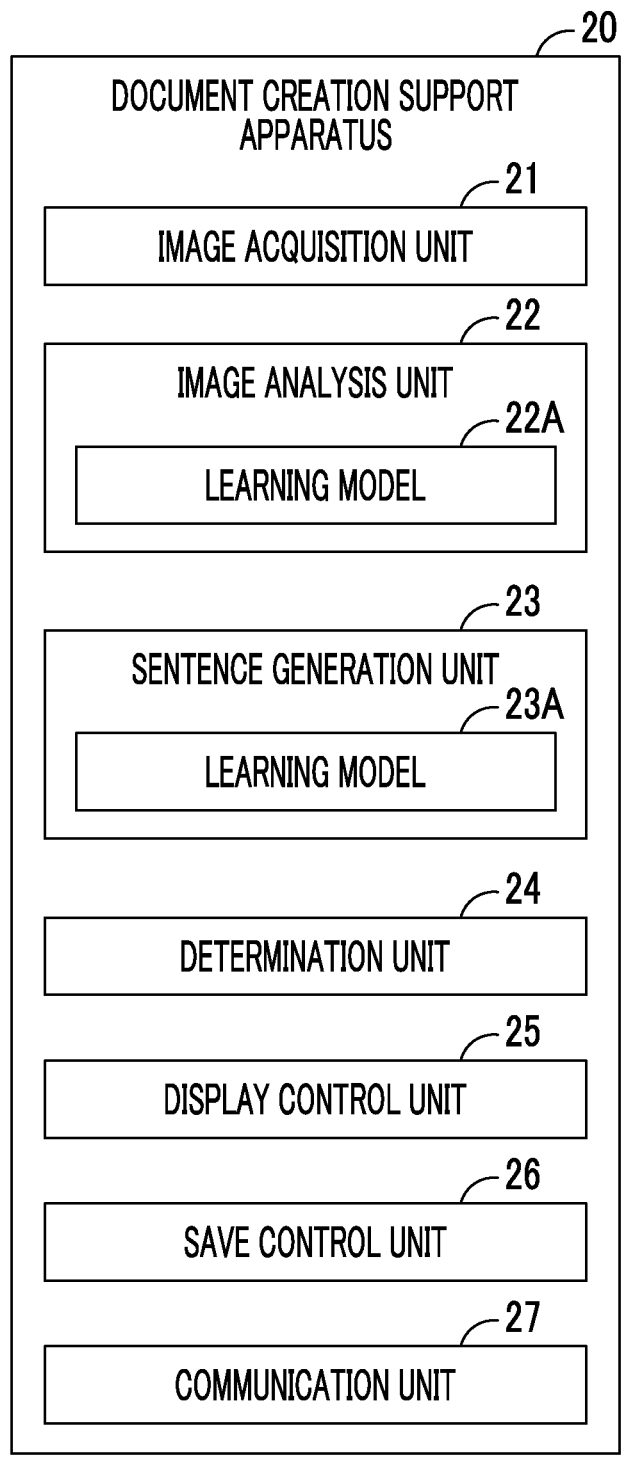
FIG. 3 is a functional configuration diagram of the document creation support apparatus according to the present embodiment.

Next, a functional configuration of the document creation support apparatus according to the present embodiment will be described. FIG. 3 is a diagram showing a functional configuration of the document creation support apparatus according to the present embodiment. As shown in FIG. 3, the document creation support apparatus 20 comprises an image acquisition unit 21, an image analysis unit 22, a sentence generation unit 23, a determination unit 24, a display control unit 25, a save control unit 26, and a communication unit 27. Then, in a case where the CPU 11 executes the document creation support program 12, the CPU 11 functions as the image acquisition unit 21, the image analysis unit 22, the sentence generation unit 23, the determination unit 24, the display control unit 25, the save control unit 26, and the communication unit 27.

The image acquisition unit 21 acquires a medical image for creating an interpretation report from the image server 5 according to an instruction from the input device 15 by the radiologist who is an operator.

The image analysis unit 22 analyzes the medical image to derive property information indicating the property of the structure of interest included in the medical image. To this end, the image analysis unit 22 has a learning model 22A in which machine learning is performed to detect an abnormal shadow included in the medical image as a structure of interest and to discriminate properties of the detected abnormal shadow for each of a plurality of predetermined property items.

Here, examples of the property item specified for the abnormal shadow include the location of the abnormal shadow, the size of the abnormal shadow, the shape of the boundary (clear and irregular), the type of absorption value (solid type and frosted glass type), the presence or absence of spicula, whether it is a tumor or a nodule, the presence or absence of pleural contact, the presence or absence of pleural invagination, the presence or absence of pleural infiltration, the presence or absence of a cavity, and the presence or absence of calcification. Note that, the examples of property items are not limited to these.

In the present embodiment, the learning model 22A consists of a convolutional neural network in which machine learning is performed through deep learning or the like using supervised training data so as to discriminate the properties of abnormal shadows in medical images.

The learning model 22A is constructed by machine learning using, for example, a plurality of combinations of a medical image including an abnormal shadow and a property item representing the property of the abnormal shadow as supervised training data. In a case where a medical image is input, the learning model 22A outputs a property score derived for each property item in the abnormal shadow included in the medical image. The property score is a score indicating the prominence of the property for each property item. The property score takes a value of 0 or more and 1 or less, for example, and the larger the value of the property score is, the more pronounced the property is.

For example, in a case where the property score for "the presence or absence of spicula", which is one of the property items of an abnormal shadow, is, for example, 0.5 or more, it is specified that the property for "the presence or absence of spicula" of the abnormal shadow is "with spicula (positive)", and in a case where the property score for "the presence or absence of spicula" is less than, for example, 0.5, it is specified that the property for the presence or absence of spicula of the abnormal shadow is "no spicula (negative)". The threshold value 0.5 used for property determination is merely an example, and is set to an appropriate value for each property item.

FIG. 4 is a diagram for describing an example of property information specified by the image analysis unit 22. As shown in FIG. 4, in property information 30 specified by the image analysis unit 22, the properties for each property item are "under left lung pleura", "4.2 cm", "irregular", "solid", "with spicula", "tumor", "with pleural contact", "with pleural invagination", "no pleural infiltration", "no cavity", and "no calcification". In FIG. 4, + is given in the case of "yes", that is, positive, and—is given in the case of "no", that is, negative.

As the learning model 22A, any learning model such as, for example, a support vector machine (SVM) can be used in addition to the convolutional neural network.

Further, the learning model for detecting the abnormal shadow from the medical image and the learning model for discriminating the property of the abnormal shadow may be constructed separately.

Figure 5:
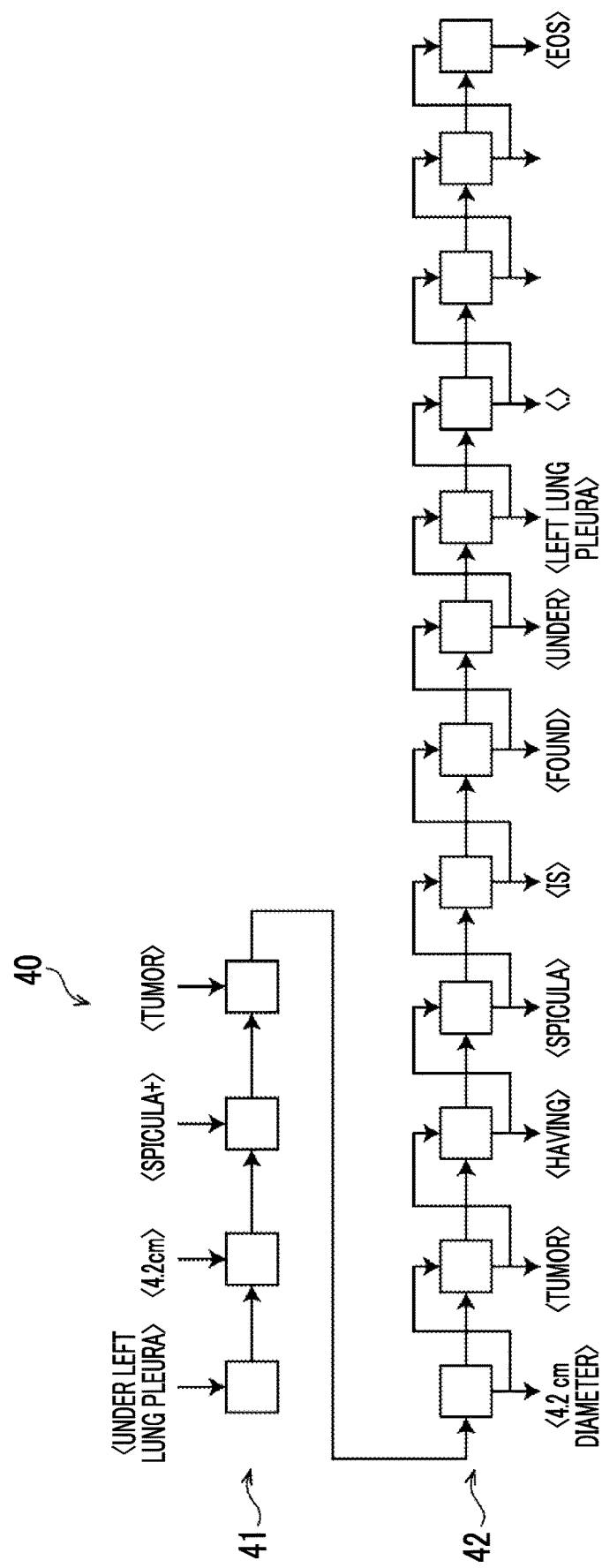
FIG. 5 is a diagram schematically showing a configuration of a recurrent neural network.

The sentence generation unit 23 generates a sentence related to a property of the abnormal shadow included in the medical image by using the property information derived by the image analysis unit 22. Further, as will be described later, a sentence amount of the generated medical sentence is adjusted according to a result of the determination performed by the determination unit 24. In the present embodiment, the sentence generation unit 23 generates a medical sentence as a sentence. The sentence generation unit 23 consists of a learning model 23A that has been trained to generate a sentence from the input information. As the learning model 23A, for example, a recurrent neural network can be used. FIG. 5 is a diagram schematically showing a configuration of a recurrent neural network. As shown in FIG. 5, a recurrent neural network 40 consists of an encoder 41 and a decoder 42. The property information derived by the image analysis unit 22 is input to the encoder 41. For example, property information indicating "under left lung pleura", "4.2 cm", "spicula+" and "tumor" is input to the encoder 41. The decoder 42 is trained to document character information, and generates a sentence from the input property information. Specifically, from the above-mentioned property information indicating "under left lung pleura", "4.2 cm", "spicula+" and "tumor", a medical sentence "A 4.2 cm diameter tumor having spicula is found under the left lung pleura" is generated. In FIG. 5, "EOS" indicates the end of the sentence (end of sentence).

In this way, in order to output the medical sentence by inputting the property information, the recurrent neural network 40 is constructed by training the encoder 41 and the decoder 42 using a large amount of supervised training data consisting of a combination of the property information and the medical sentence.

The sentence generation unit 23 adjusts a sentence amount such that a sentence amount of the medical sentence is a prescribed amount based on the result of the determination performed by the determination unit 24, which will be described later. The adjustment of the sentence amount will be described later.

The determination unit 24 determines whether or not the sentence amount of the medical sentence generated by the sentence generation unit 23 is a prescribed amount. Specifically, the determination unit 24 determines the sentence amount by determining whether or not the number of characters, the number of lines, or the number of paragraphs of the sentence is a prescribed amount Th1. The prescribed amount Th1 may be a constant value or a value having a range. In a case where the prescribed amount is a value having a range, the range may have only an upper limit value, may have only a lower limit value, or may have both an upper limit value and a lower limit value. Specifically, in a case of the number of characters, the prescribed amount Th1 may be 100 characters, 100 characters or more, 100 characters or less, or 90 characters or more and 110 characters or less. In the present embodiment, the prescribed amount Th1 will be described as a value having an upper limit value and a lower limit value. In addition, the prescribed amount Th1 may be changed according to the preference of the radiologist.

Then, in a case where the sentence amount of the medical sentence generated by the sentence generation unit 23 is not the prescribed amount Th1, the determination unit 24 gives an instruction according to the determination result to the sentence generation unit 23. That is, in a case where the sentence amount is less than the prescribed amount Th1, an instruction to increase the sentence amount is given, and in a case where the sentence amount is larger than the prescribed amount Th1, an instruction to reduce the sentence amount is given. In a case where the sentence amount of the medical sentence generated by the sentence generation unit 23 is the prescribed amount Th1, the determination unit 24 does nothing.

The sentence generation unit 23 adjusts the sentence amount of the medical sentence according to the instruction from the determination unit 24. FIG. 6 is a diagram showing an example of medical sentences and medical sentences in which a sentence amount is adjusted. As shown in FIG. 6, it is assumed that medical sentences 51 before adjustment are "A 21 mm-sized irregular solid nodule is found in the left lower lobe S6. It is lobular and has a clear boundary. Calcification is found inside, but cavities and air bronchograms are not included. The nodule is in contact with the pleura." In a case where the determination unit 24 gives an instruction to reduce the sentence amount with respect to the medical sentences 51, the sentence generation unit 23 adjusts the sentence amount by selecting the property to be described in the medical sentence. For example, the sentence amount is adjusted by selecting only the shape-related properties from among the plurality of properties included in the medical sentences 51, and a medical sentence 52 of "A 21 mm-sized irregular solid nodule is found in the left lower lobe S6" is generated. Alternatively, properties other than the properties related to the inside such as calcification, cavities, and air bronchograms in the medical sentences 51, and the properties related to contact with other tissues such as pleural contact may be selected. In this case, the sentence generation unit 23 adjusts the sentence amount of the medical sentences 51 to generate medical sentences 53 of "A 21 mm-sized irregular solid nodule is found in the left lower lobe S6. It is lobular and has a clear boundary."

Further, the sentence generation unit 23 may adjust the sentence amount by selecting only the positive properties in the medical sentences 51. In this case, the sentence generation unit 23 adjusts the sentence amount of the medical sentences 51 to generate medical sentences 54 of "A 21 mm-sized irregular solid nodule is found in the left lower lobe S6. It is lobular and has a clear boundary. Calcification is found inside. The nodule is in contact with the pleura."

In a case where the medical sentence is too short, the sentence generation unit 23 adjusts the sentence amount of the medical sentence so as to increase the sentence amount. For example, as shown in FIG. 7, in a case where a medical sentence 61 before adjustment is "A 21 mm-sized irregular solid nodule is found in the left lower lobe S6", the sentence amount of the medical sentence 61 is adjusted by selecting all the positive property items derived by the image analysis unit 22. For example, the sentence generation unit 23 adjusts the sentence amount of the medical sentence 61 to generate medical sentences 62 of "A 21 mm-sized irregular solid nodule is found in the left lower lobe S6. It is lobular and has a clear boundary. Calcification is found inside. The nodule is in contact with the pleura." In addition, the sentence generation unit 23 may adjust the sentence amount of the medical sentence 61 so as to select all of the negative property item and the positive property item. For example, the sentence generation unit 23 adjusts the sentence amount of the medical sentence 61 to generate medical sentences 63 of "A 21 mm-sized irregular solid nodule is found in the left lower lobe S6. It is lobular and has a clear boundary. Calcification is found inside, but cavities and air bronchograms are not included. The nodule is in contact with the pleura."

Here, in a case where the medical image includes a plurality of abnormal shadows, the sentence generation unit 23 generates a medical sentence including a description regarding each of the properties specified for the plurality of abnormal shadows. In such a case, in a case where the determination unit 24 gives an instruction to reduce the sentence amount, the sentence generation unit 23 may adjust the sentence amount by integrating the common descriptions among the descriptions regarding each of the properties specified for the plurality of abnormal shadows. For example, as shown in FIG. 8, it is assumed that medical sentences 65 before adjustment are "There is a solid nodule with irregularities in the left lung S3. It is accompanied by spicula. In addition, there is a solid nodule with irregularities in the right lung S7", and descriptions regarding two abnormal shadows are included. In this case, the description regarding the solid nodule is common to the two abnormal shadows. Therefore, the sentence generation unit 23 adjusts the sentence amount by integrating the descriptions regarding the solid nodules common to the two abnormal shadows to generate a medical sentence 66 of "There are solid nodules with irregularities in the left lung S3 and the right lung S7."

Further, in a case where the medical image includes a plurality of abnormal shadows, the sentence generation unit 23 may generate a plurality of candidate sentences describing properties of each of abnormal shadows, and adjust, for each of the plurality of abnormal shadows, the sentence amount by selecting a combination in which a sentence amount of a sentence including a selected candidate sentence is the prescribed amount from combinations of selecting one candidate sentence from among the plurality of candidate sentences.

For example, in a case where the medical image includes two abnormal shadows A and B, as shown in FIG. 9, the sentence generation unit 23 generates candidate sentences 71A to 71C for the abnormal shadow A and candidate sentences 72A to 72C for the abnormal shadow B, respectively. Then, the sentence generation unit 23 selects one candidate sentence from each of the candidate sentences 71A to 71C for the abnormal shadow A and the candidate sentences 72A to 72C for the abnormal shadow B to generate a medical sentence. For example, the candidate sentence 71C for the abnormal shadow A and the candidate sentence 72C for the abnormal shadow B are selected to generate medical sentences 73 shown in FIG. 10.

In a case where the sentence amount of the medical sentences 73 is larger than a prescribed amount, the determination unit 24 gives an instruction to shorten the sentence amount. Thereby, the sentence generation unit 23 performs adjustment so as to reduce the sentence amount of the medical sentences 73, and generates medical sentences 74. At this time, the sentence generation unit 23 may select the candidate sentence such that the description regarding the abnormal shadow having a higher degree of malignancy among the abnormal shadows A and B becomes longer. For example, in the abnormal shadow A and the abnormal shadow B, the abnormal shadow A has a higher degree of malignancy. Therefore, the medical sentences 74 are generated by changing the description regarding the abnormal shadow B included in the medical sentences 73 to the candidate sentence 72A shorter than the candidate sentence 72C.

Further, as described above, the sentence amount of the medical sentences 73 may be adjusted by selecting only the negative properties from among the descriptions included in the medical sentences 73 or by integrating the descriptions of the common properties.

In addition, the medical image and the interpretation report acquired in the past for the same patient may be acquired, it may be determined whether the abnormal shadow included in the medical image to be interpreted at the present is a continuation of the past medical image or a newly appearing abnormal shadow, and the description of the newly appearing abnormal shadow may be lengthened.

Figure 11:
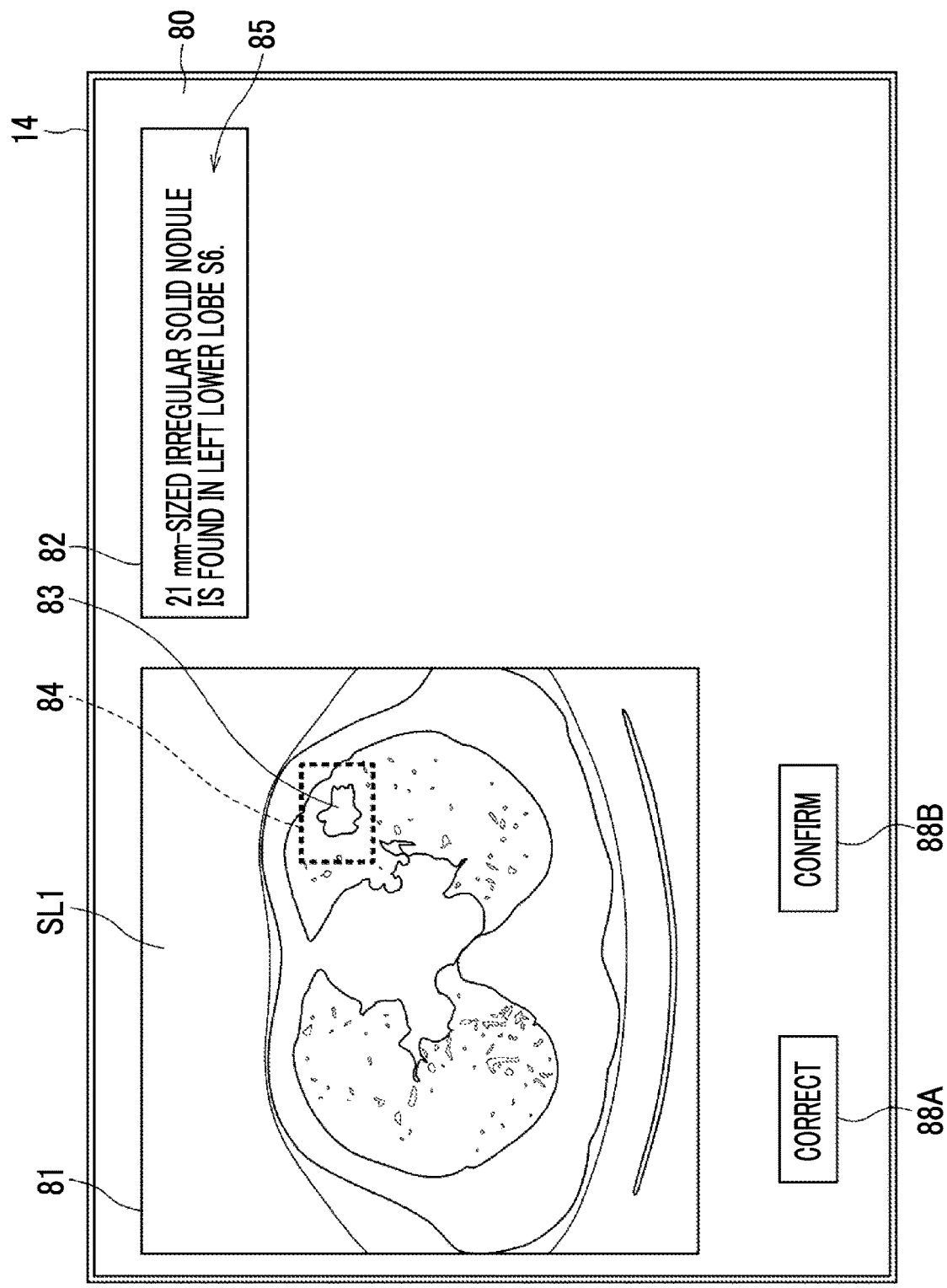
FIG. 11 is a diagram showing an example of a display screen of a medical sentence.

The display control unit 25 displays the generated medical sentence on the display 14. FIG. 11 is a diagram showing a display screen of a medical sentence. As shown in FIG. 11, a display screen 80 includes an image display region 81 and a sentence display region 82. In the image display region 81, a slice image SL1 that is most likely to specify the abnormal shadow detected by the image analysis unit 22 is displayed. The slice image SL1 includes an abnormal shadow 83, and the abnormal shadow 83 is surrounded by a rectangular region 84.

In the sentence display region 82, a medical sentence 85 which is generated by the sentence generation unit 23 or in which a sentence amount is adjusted is displayed. The medical sentence 85 is the same as the medical sentence 52 shown in FIG. 6, "A 21 mm-sized irregular solid nodule is found in the left lower lobe S6."

Below the image display region 81, a correction button 88A and a confirmation button 88B are displayed.

The radiologist interprets the slice image SL1 displayed in the image display region 81 and included in the medical image, and determines the suitability of the medical sentence 85 displayed in the sentence display region 82. By selecting the correction button 88A, the radiologist can manually correct the medical sentence 85 displayed in the sentence display region 82 by input from the input device 15. Further, by selecting the confirmation button 88B, the medical sentence 85 displayed in the sentence display region 82 can be confirmed with its contents.

By the selection of the confirmation button 88B performed by the operator, the save control unit 26 transcribes the medical sentence 85 described in the sentence display region 82 to the interpretation report, and saves the interpretation report and the slice image referred to in the case of generating the interpretation report together in the storage 13.

The communication unit 27 transfers the interpretation report to which the medical sentence 85 described in the sentence display region 82 is transcribed and the slice image referred to in the case of generating the interpretation report together to the report server 7 via the network I/F 17. The report server 7 saves the interpretation report and the slice image together.

Figure 12:
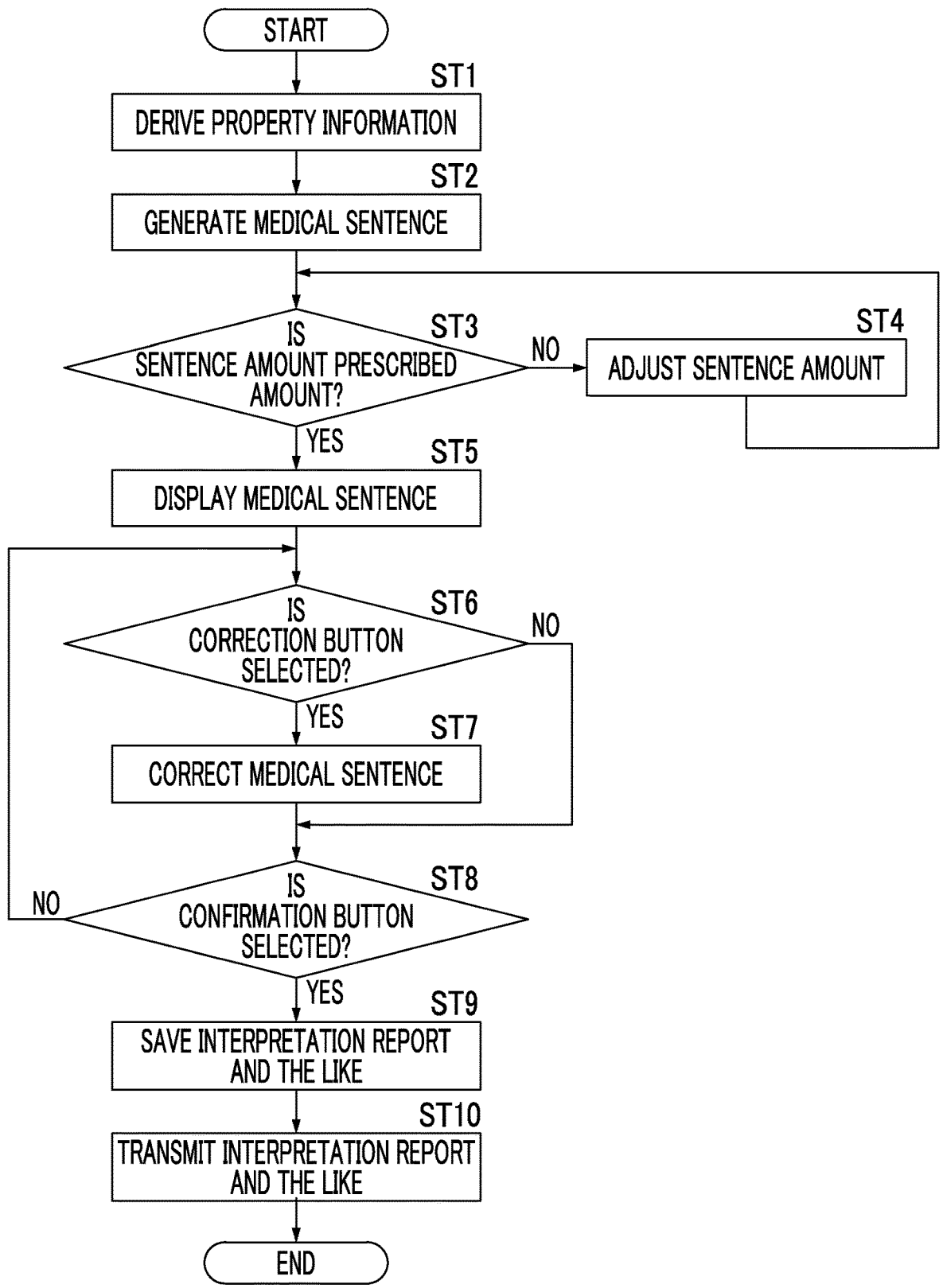
FIG. 12 is a flowchart showing a process performed in the present embodiment.

Next, a process performed in the present embodiment will be described. FIG. 12 is a flowchart showing a process performed in the present embodiment. It is assumed that the medical image to be interpreted is acquired from the image server 5 by the image acquisition unit 21 and is saved in the storage 13. The process is started in a case where an instruction to create an interpretation report is given by the radiologist, and the image analysis unit 22 analyzes the medical image to derive property information indicating the property of the structure of interest such as an abnormal shadow included in the medical image (Step ST1). Next, the sentence generation unit 23 generates a medical sentence related to the medical image based on the property information (Step ST2). Subsequently, the determination unit 24 determines whether or not the sentence amount of the generated medical sentence is a prescribed amount (Step ST3).

In a case where Step ST3 is negative, the sentence generation unit 23 adjusts the sentence amount such that the sentence amount of the medical sentence is the prescribed amount based on a result of the determination (Step ST4), and returns to Step ST3. In a case where Step ST3 is affirmative, the display control unit 25 displays the medical image and the medical sentence generated by the sentence generation unit 23 on the display 14 (Step ST5).

Next, the display control unit 25 determines whether or not the correction button 88A displayed on the display screen is selected (Step ST6). In a case where Step ST6 is affirmative, the display control unit 25 receives the correction of the medical sentence displayed in the sentence display region 82 using the input device 15, and the sentence generation unit 23 corrects the medical sentence displayed in the sentence display region 82 by input from the input device 15 (Step ST7). Subsequently, the display control unit 25 determines whether or not the confirmation button 88B is selected (Step ST8). In a case where Step ST8 is negative, the process returns to Step ST6.

In a case where Step ST8 is affirmative, the save control unit 26 transcribes the medical sentence to the interpretation report for the medical image, and saves the interpretation report and the medical image together in the storage 13 (saving the interpretation report or the like; Step ST9). Then, the communication unit 27 transfers the interpretation report and the medical image together to the report server 7 via the network I/F 17 (transfer of the interpretation report or the like; Step ST10), and ends the process.

In this way, in the present embodiment, it is determined whether or not the sentence amount of the sentence is the prescribed amount, and the sentence amount is adjusted such that the sentence amount is the prescribed amount based on the determination result. Therefore, it is possible to generate medical sentences with an appropriate amount of information.

Figure 13:
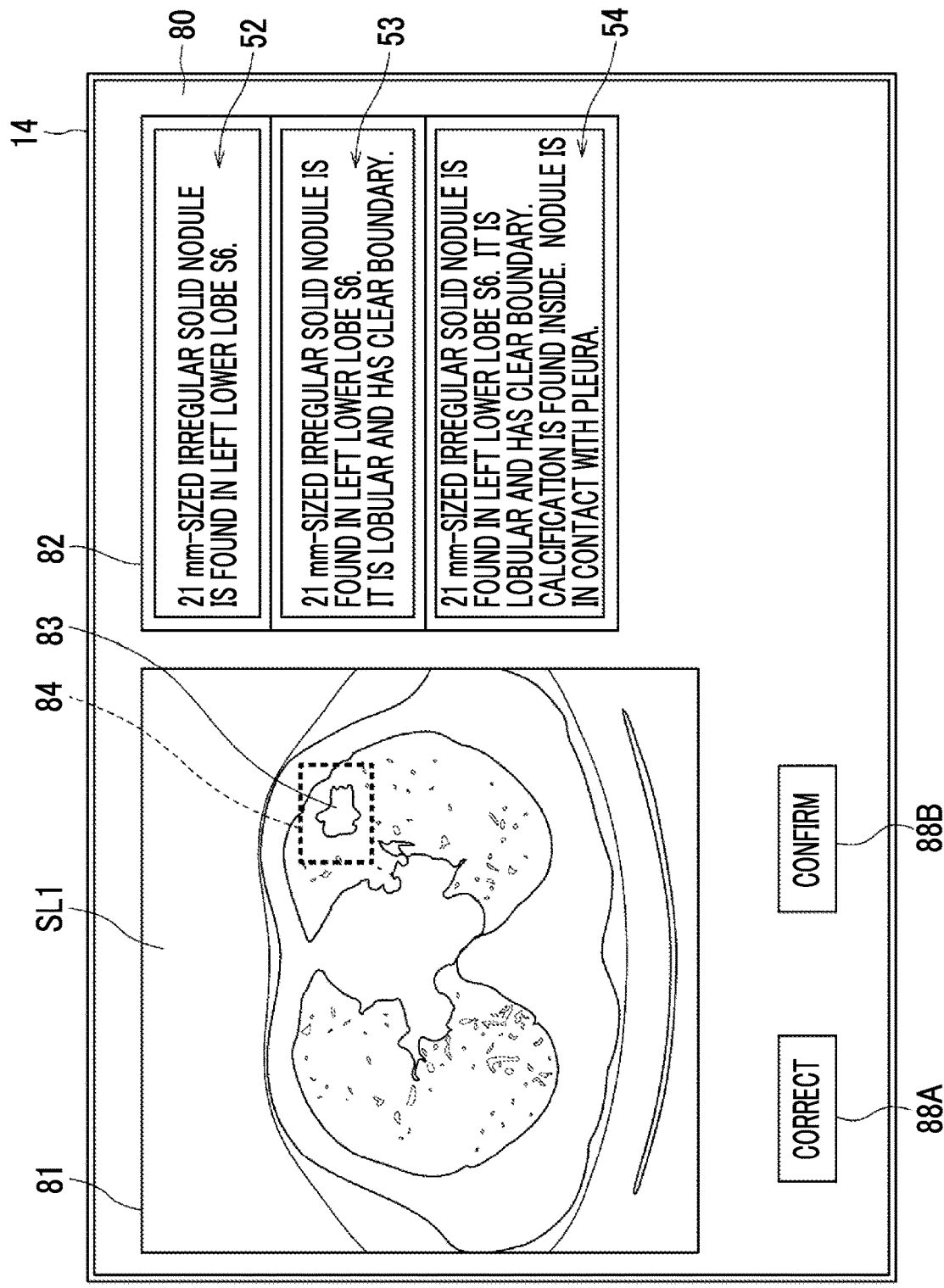
FIG. 13 is a diagram showing another example of a display screen of a medical sentence.
Figure 14:
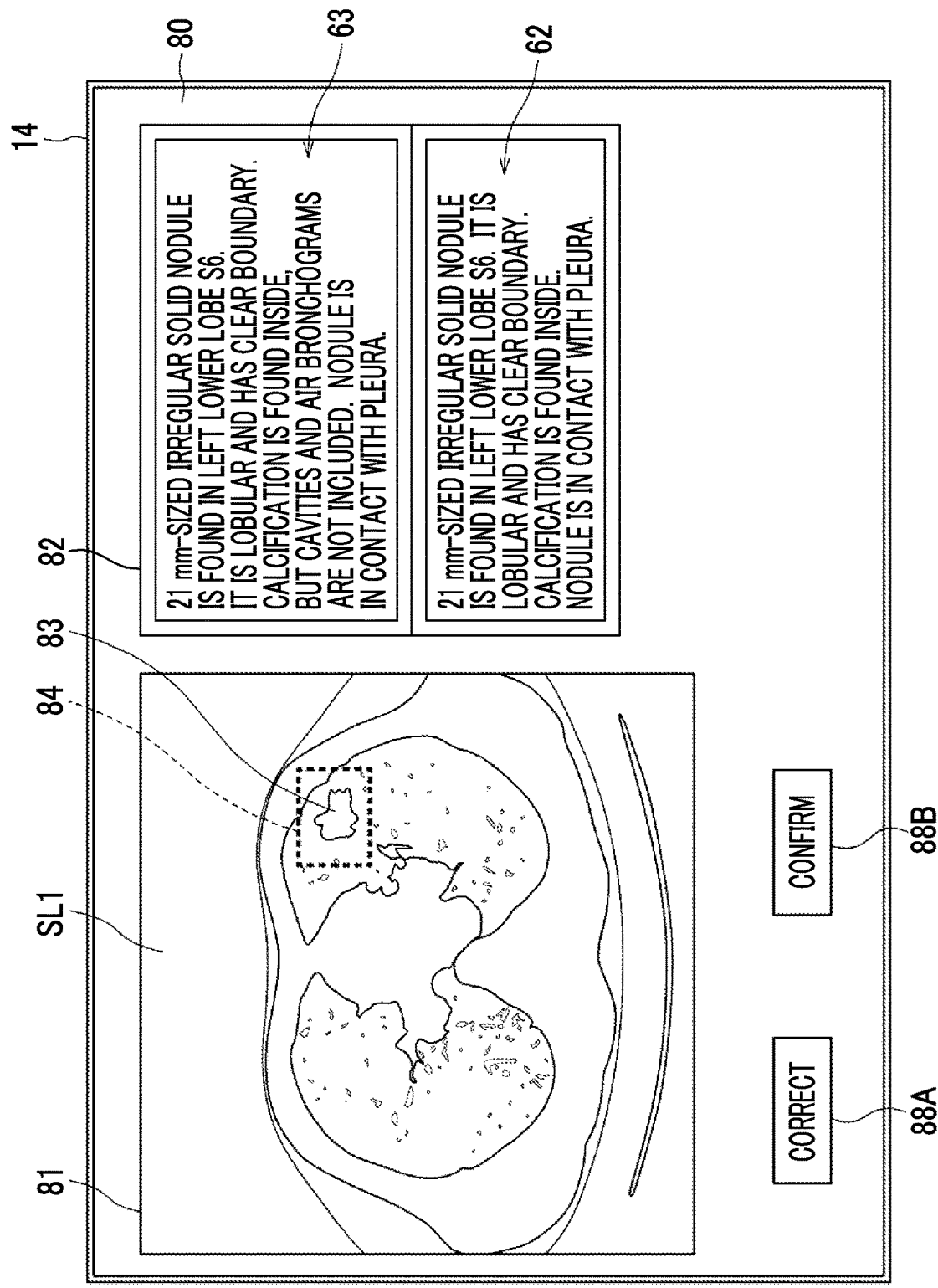
FIG. 14 is a diagram showing another example of a display screen of a medical sentence.

In the above embodiment, one medical sentence in which the sentence amount is adjusted to the prescribed amount is displayed in the sentence display region 82 of the display screen 80, but the present disclosure is not limited thereto. For example, as shown in FIG. 13, three medical sentences 52 to 53 shown in FIG. 6 may be displayed in the sentence display region 82, and from among the displayed medical sentences 52 to 53, the medical sentence desired by the radiologist may be selected by using the input device 15. In FIG. 13, the medical sentences 52 to 54 are displayed in ascending order of the sentence amount from the top. Further, since the medical sentence generated by the sentence generation unit 23 is short, in a case where the sentence amount of the medical sentence is adjusted to increase, a plurality of medical sentences may be displayed in descending order of the sentence amount. For example, as shown in FIG. 14, the medical sentences 62 and 63 shown in FIG. 7 may be displayed in the order of the medical sentences 63 and 62 from the top.

Further, in the above embodiment, the technique of the present disclosure is applied in the case of creating an interpretation report using a medical image with the lung as the diagnosis target, but the diagnosis target is not limited to the lung. In addition to the lung, any part of a human body such as a heart, liver, brain, and limbs can be diagnosed.

Further, in the above embodiment, for example, as hardware structures of processing units that execute various kinds of processing, such as the image acquisition unit 21, the image analysis unit 22, the sentence generation unit 23, the determination unit 24, the display control unit 25, the save control unit 26, and the communication unit 27, various processors shown below can be used. As described above, the various processors include a programmable logic device (PLD) as a processor of which the circuit configuration can be changed after manufacture, such as a field programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (programs).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor.

As an example where a plurality of processing units are configured by one processor, first, there is a form in which one processor is configured by a combination of one or more CPUs and software as typified by a computer, such as a client or a server, and this processor functions as a plurality of processing units. Second, there is a form in which a processor for realizing the function of the entire system including a plurality of processing units via one integrated circuit (IC) chip as typified by a system on chip (SoC) or the like is used. In this way, various processing units are configured by one or more of the above-described various processors as hardware structures.

Furthermore, as the hardware structure of the various processors, more specifically, an electrical circuit (circuitry) in which circuit elements such as semiconductor elements are combined can be used.

What is claimed is:

1. A document creation support apparatus comprising at least one processor, wherein the processor is configured to:
   analyze a medical image to detect at least one structure of interest included in the medical image and to derive property information indicating a plurality of properties of the at least one structure of interest;
   generate a sentence based on a first portion of the properties;
   determine whether or not a sentence amount of the sentence is a prescribed amount; and
   in response to a determination of the sentence amount of the sentence not being the prescribed amount, adjust, without user interaction, the sentence amount to generate a new sentence by either reducing or increasing the sentence to satisfy the prescribed amount,
   wherein the processor increases the sentence amount of the sentence by using a second portion of the properties, wherein the second portion is larger than the first portion, and wherein the first portion is included in the second portion,
   wherein the processor reduces the sentence amount of the sentence by using a third portion of the properties, wherein the third portion is smaller than the first portion, and wherein the third portion is included in the first portion.

2. The document creation support apparatus according to claim 1, wherein the processor is configured to adjust the sentence amount by selecting a property to be described in the sentence from among one or more properties of the at least one structure of interest.

3. The document creation support apparatus according to claim 1, wherein the processor is configured to generate the sentence including a description regarding each of one or more properties specified for the at least one structure of interest, and adjust the sentence amount by deleting, from the sentence, a description regarding a negative property among descriptions regarding each of a plurality of properties included in the sentence.

4. The document creation support apparatus according to claim 1, wherein the processor is configured to
   generate, for a plurality of structures of interest included in the image, a plurality of sentences describing properties of each of the plurality of structures of interest, and
   adjust the sentence amount of the sentence for at least one of the plurality of structures of interest such that a total amount of the sentence generated for each of the plurality of structures of interest is the prescribed amount.

5. The document creation support apparatus according to claim 4, wherein the processor is configured to adjust the sentence amount by integrating common descriptions among the descriptions regarding each of the plurality of structures of interest included in the sentence.

6. The document creation support apparatus according to claim 1, wherein the processor is configured to
   generate, for a plurality of structures of interest included in the image, a plurality of candidate sentences describing properties of each of the plurality of structures of interest, and
   adjust, for each of the plurality of structures of interest, the sentence amount by selecting a combination in which a sentence amount of a sentence including a selected candidate sentence is the prescribed amount from combinations of selecting one candidate sentence from among the plurality of candidate sentences.

7. The document creation support apparatus according to claim 1, wherein the processor is configured to display the sentence on a display.

8. A document creation support method comprising:
   analyzing a medical image to detect at least one structure of interest included in the medical image and to derive property information indicating a plurality of properties of the at least one structure of interest;
   generating a sentence based on a first portion of the properties;
   determining whether or not a sentence amount of the sentence is a prescribed amount; and
   in response to a determination of the sentence amount of the sentence not being the prescribed amount, adjusting, without user interaction, the sentence amount to generate a new sentence by either reducing or increasing the sentence to satisfy the prescribed amount,
   wherein the sentence amount of the sentence is increased by using a second portion of the properties, wherein the second portion is larger than the first portion, and wherein the first portion is included in the second portion,
   wherein the sentence amount of the sentence is reduced by using a third portion of the properties, wherein the third portion is smaller than the first portion, and wherein the third portion is included in the first portion.

9. A non-transitory computer-readable storage medium that stores a document creation support program causing a computer to execute a procedure comprising:
   analyzing a medical image to detect at least one structure of interest included in the medical image and to derive property information indicating a plurality of properties of the at least one structure of interest;
   generating a sentence based on a first portion of the properties;

determining whether or not a sentence amount of the sentence is a prescribed amount; and in response to a determination of the sentence amount of the sentence not being the prescribed amount, adjusting, without user interaction, the sentence amount to generate a new sentence by either reducing or increasing the sentence to satisfy the prescribed amount, wherein the sentence amount of the sentence is increased by using a second portion of the properties, wherein the second portion is larger than the first portion, and wherein the first portion is included in the second portion, wherein the sentence amount of the sentence is reduced by using a third portion of the properties, wherein the third portion is smaller than the first portion, and wherein the third portion is included in the first portion.

\* \* \* \* \*